United States Patent [19]
Imran et al.

[11] Patent Number: 5,766,203
[45] Date of Patent: Jun. 16, 1998

[54] SHEATH WITH EXPANDABLE DISTAL EXTREMITY AND BALLOON CATHETERS AND STENTS FOR USE THEREWITH AND METHOD

[75] Inventors: Mir A. Imran, Palo Alto; Deepak R. Gandhi, San Jose; Anant V. Hegde; Gholam-Reza Zadno-Azizi, both of Newark, all of Calif.

[73] Assignee: Intelliwire, Inc., Sunnyvale, Calif.

[21] Appl. No.: 728,769

[22] Filed: Oct. 10, 1996

Related U.S. Application Data

[63] Continuation of Ser. No. 504,929, Jul. 20, 1995, abandoned.

[51] Int. Cl.⁶ .................................................. A61M 29/00
[52] U.S. Cl. .................. 606/198; 606/108; 606/191; 606/192; 606/194; 606/195; 606/200; 604/96; 623/1; 623/12
[58] Field of Search .................................. 606/108, 191, 606/192, 194, 195, 198, 200; 623/1, 12; 604/96

[56] References Cited

U.S. PATENT DOCUMENTS

| 1,271,456 | 7/1918 | Flack | 606/198 |
|---|---|---|---|
| 3,970,089 | 7/1976 | Saice | 604/256 |
| 4,998,539 | 3/1991 | Delsanti | 606/194 X |
| 5,026,377 | 6/1991 | Burton et al. | 606/108 |
| 5,116,318 | 5/1992 | Hillstead | 606/194 |
| 5,123,917 | 6/1992 | Lee | 623/1 |
| 5,160,321 | 11/1992 | Sahota | 606/192 |
| 5,196,024 | 3/1993 | Barath | 606/194 |
| 5,250,070 | 10/1993 | Parodi | 606/194 |
| 5,320,634 | 6/1994 | Vigil et al. | 606/159 |
| 5,356,382 | 10/1994 | Picha et al. | 606/198 X |
| 5,443,449 | 8/1995 | Buelna | 606/192 |
| 5,453,090 | 9/1995 | Martinez et al. | 606/108 |
| 5,478,349 | 12/1995 | Nicholas | 606/198 |

FOREIGN PATENT DOCUMENTS

| 073751 | 9/1917 | Austria | 606/198 |
|---|---|---|---|

*Primary Examiner*—Michael Powell Buiz
*Assistant Examiner*—Daphna Shai
*Attorney, Agent, or Firm*—Flehr Hohbach Test Albritton & Herbert LLP

[57] ABSTRACT

A sheath for advancement into a vessel of a patient having a stenosis therein which at least partially occludes the flow of blood in the vessel. A flexible elongate tubular member has proximal and distal extremities with a lumen extending from the proximal extremity to the distal extremity. A portion of the distal extremity of the flexible elongate tubular member is radially expandable. The expandable portion carries stiffening elements that impart pushability and column strength to the expandable portion.

23 Claims, 4 Drawing Sheets

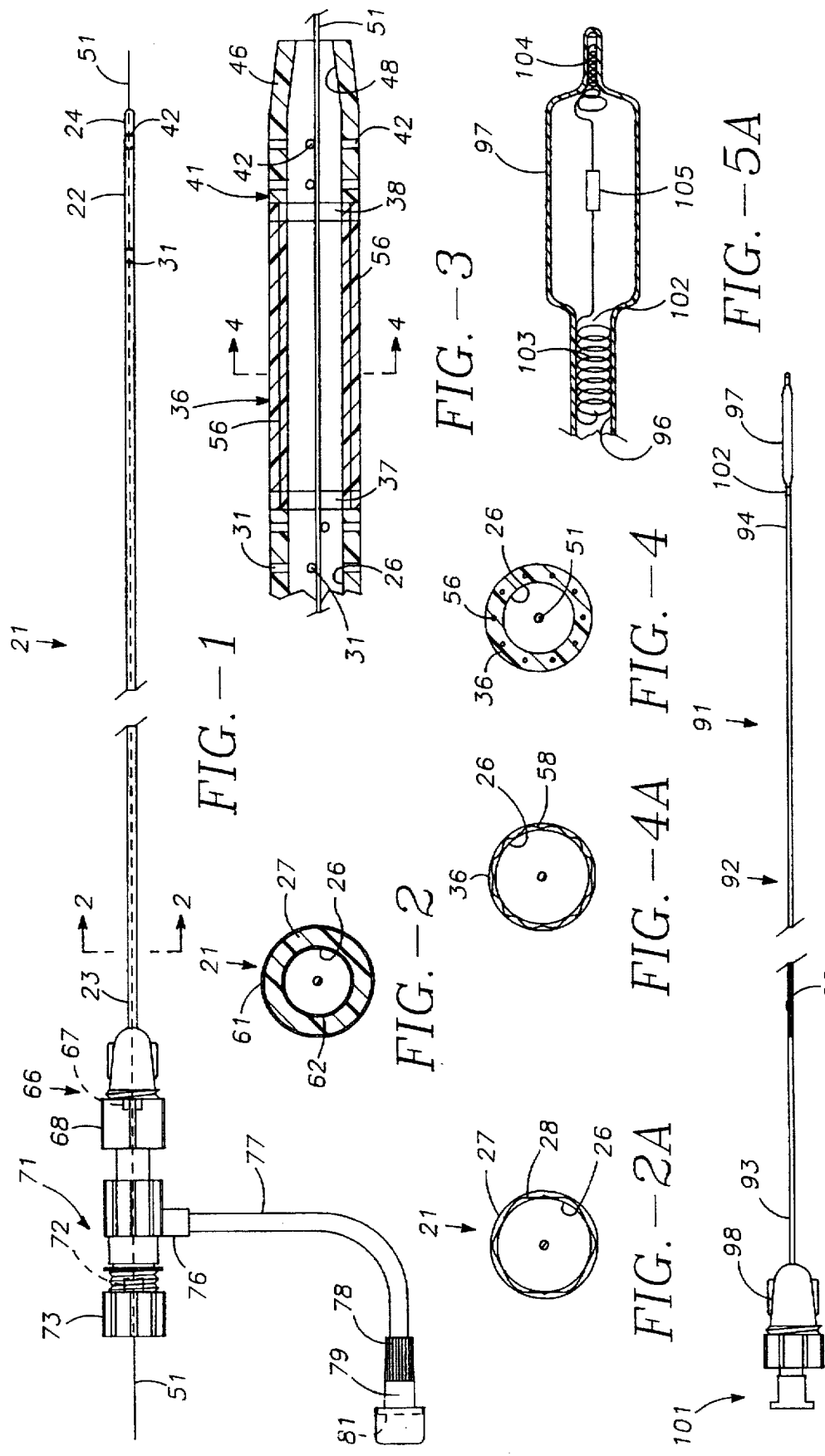

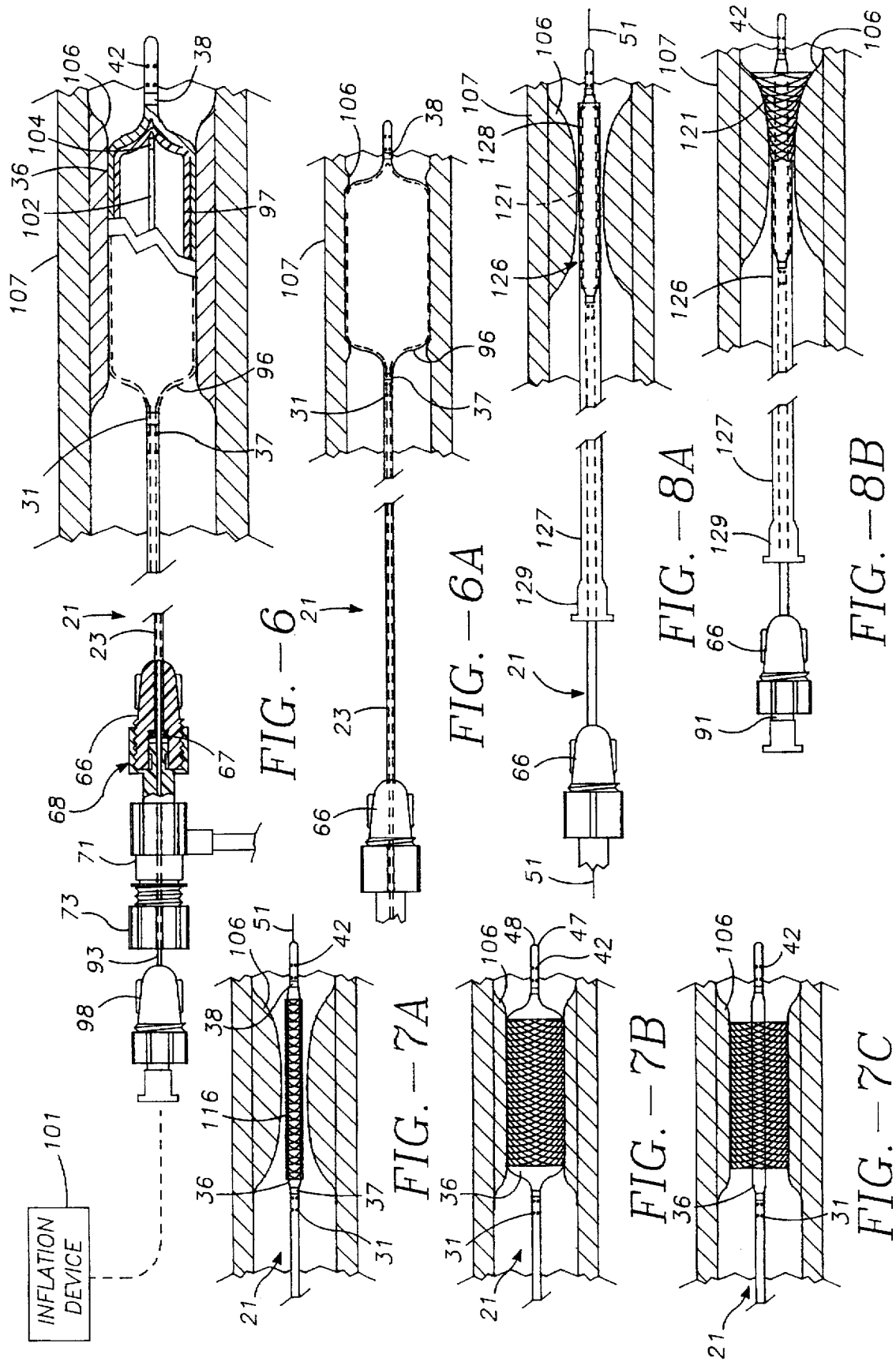

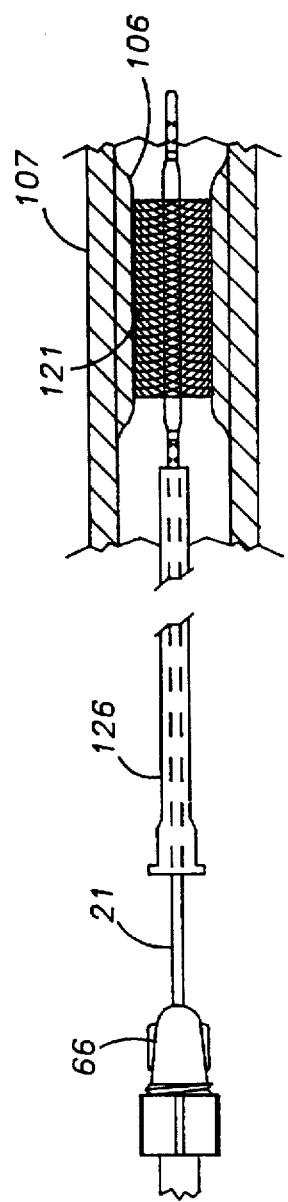
FIG.–8C
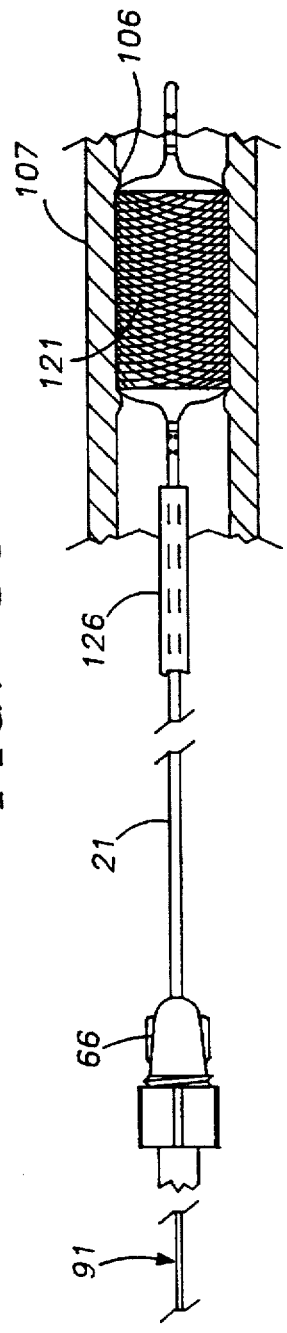
FIG.–8D
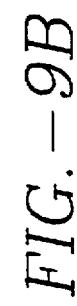
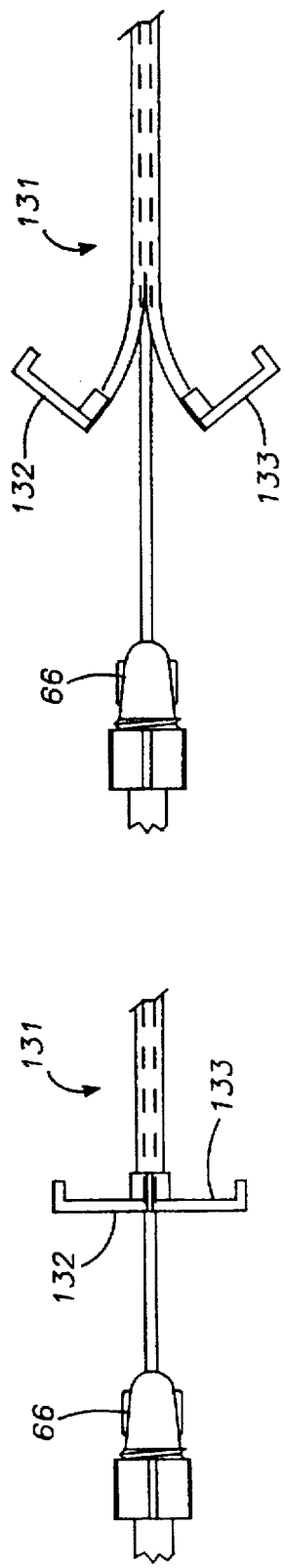
FIG.–9A
FIG.–9B

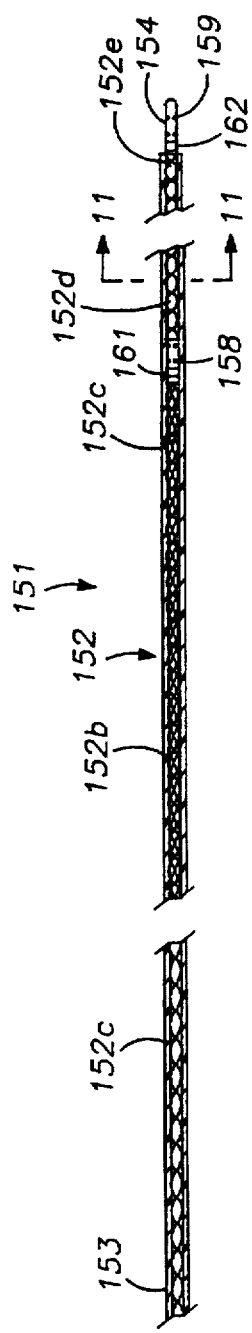
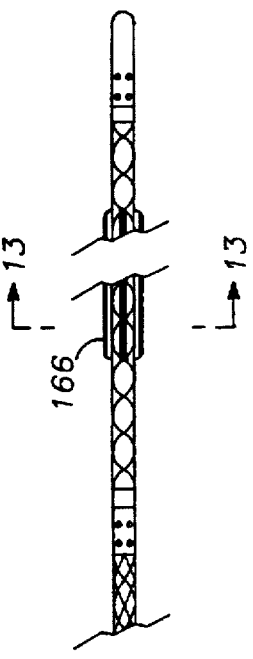
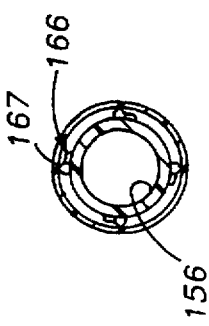
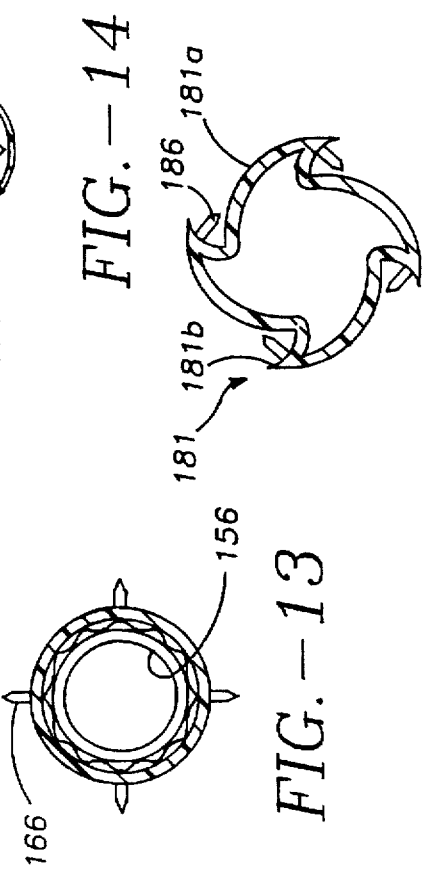
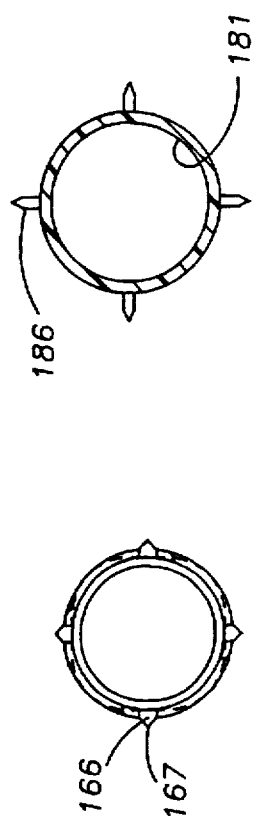
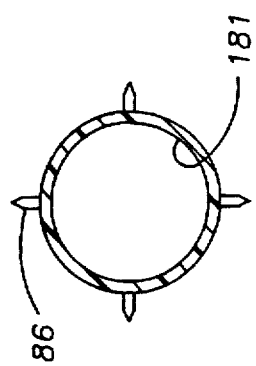
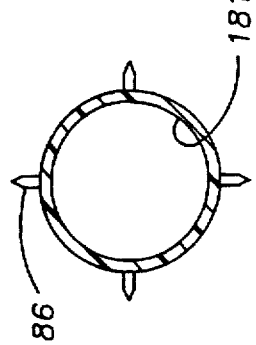

SHEATH WITH EXPANDABLE DISTAL EXTREMITY AND BALLOON CATHETERS AND STENTS FOR USE THEREWITH AND METHOD

This is a continuation of application Ser. No. 08/504,929 filed Jul. 20, 1995 now abandoned.

This invention relates to a sheath with expandable distal extremity and balloon catheters and stents for use therewith and particularly for creating larger openings or passageways through stenoses in the vessels of a human being.

In the past in providing larger passageways through stenoses in the vessels of the human body, it has been the practice to use angioplasty balloon catheters of increasingly larger sizes to treat such stenosis and to use rapid deployment techniques for use therewith. The use of such a plurality of angioplasty balloon catheters has been expensive and time consuming. There is therefore need for a new and improved apparatus and method which overcomes these difficulties.

In general, it is an object of the present invention to provide a sheath with an expandable extremity and balloon catheters and stents for use therewith and a method which can be utilized for treating stenoses or occlusions in vessels in a living body.

Another object of the invention is to provide a sheath and method of the above character which makes it possible to utilize simplified balloon catheters for obtaining various sizes of expansions of the distal extremity of the sheath.

Another object of the invention is to provide a sheath and method of the above character which has perfusion capabilities.

Another object of the invention is to provide a sheath and method of the above character which facilitates rapid exchange of balloon catheters.

Another object of the invention is to provide a sheath and method of the above character which facilitates the deployment of stents.

Another object of the invention is to provide a sheath and method of the above character which facilitates cutting or breaking up of the stenosis.

Another object of the invention is to provide a sheath and method of the above character in which the sheath is provided with the pushability characteristics.

Another object of the invention is to provide a sheath and method of the above character in which the expandable portion is also provided with the pushability characteristics.

Another object of the invention is to provide a sheath and method of the above character which has torquable characteristics.

Another object of the invention is to provide a sheath and method of the above character with balloon catheters and stents for use therewith which can be manufactured economically.

Additional objects and features of the invention will appear from the following description in which the preferred embodiments are set forth in conjunction with the accompanying drawings.

FIG. 1 is a side-elevational view of a sheath with an expandable distal extremity incorporating the present invention.

FIG. 2 is an enlarged cross-sectional view taken along the line 2—2 of FIG. 1.

FIG. 2A is an enlarged cross-sectional view similar to FIG. 2 but showing another embodiment of the sheath as shown in FIG. 1.

FIG. 3 is a large cross-sectional view of the distal extremity of the sheath shown in FIG. 1.

FIG. 4 is a cross-sectional view taken along the line 4—4 of FIG. 3.

FIG. 4A is a large cross-sectional view similar to FIG. 4 but showing another embodiment of the sheath of the present invention.

FIG. 5 is a side-elevational view of a balloon catheter for use with the sheath with expandable distal extremity shown in FIG. 1.

FIG. 5A is an enlarged sectional view of the distal extremity of the balloon catheter shown in FIG. 5.

FIG. 6 is an enlarged side-elevational view of the proximal and distal extremities of the combination of the sheath incorporating the present invention with a balloon catheter of the type shown in FIG. 5 utilized in enlarging the passageway through a stenosis in a vessel of a patient.

FIG. 6A is an enlarged cross-sectional view of the distal extremities of the assembly shown in FIG. 6 but showing a larger size balloon catheter creating a larger passageway through the stenosis after a rapid exchange of balloon catheters.

FIG. 7A is a side-elevational view of the distal extremity of a sheath incorporating the present invention being utilized for delivering a stent into the stenosis in a vessel of a patient.

FIG. 7B is a side-elevational view similar to that shown in FIG. 7A but showing the sheath with an expanded distal extremity to expand the stent to the stenosis.

FIG. 7C is a side-elevational view similar to FIGS. 7A and 7B but showing the distal extremity of the sheath returned to its unexpanded shape and leaving the stent in place.

FIG. 8A is a partial side-elevational view showing the sheath of the present invention being utilized for delivering a self-expanding stent into a stenosis and in which the self-expanding stent is covered by a sheath.

FIG. 8B is a side-elevational view showing the assembly in FIG. 8A with the sheath being partially retracted and with the self-expanding stent having its distal extremity expanded.

FIG. 8C is a side-elevational view similar to FIG. 8B but showing the sheath completely retracted from the self-expanding stent and the self-expanding stent expanded to engage the stenosis in the vessel to retain the passageway through the stenosis.

FIG. 8D is a side-elevational view similar to that shown in FIG. 8C but showing the use of a balloon catheter in the sheath to expand the self-expanding stent to enlarge the passageway through the stenosis.

FIG. 9A is a side-elevational view similar to that shown in FIG. 8 but showing a splittable sleeve as an alternative to the sleeve shown in FIG. 8A.

FIG. 9B is a view similar to that shown in FIG. 9A but showing the splittable sleeve being split apart to remove the same from the sheath.

FIG. 10 is another embodiment of a sheath incorporating the present invention with cutting blades provided on the expandable distal extremity.

FIG. 11 is a cross-sectional view taken along the line 11—11 of FIG. 10.

FIG. 12 is an enlarged view of a portion of the sheath shown in FIG. 10 with the cutting blades in extended positions.

FIG. 13 is a cross-sectional view taken along the line 13—13 of FIG. 12.

FIG. 14 is a cross-sectional view of another embodiment of a sheath of the present invention shown in FIG. 10 but with the cutting blades in recessed positions.

FIG. 15 is a cross-sectional view similar to FIG. 14 but showing the cutting blades extended.

3

FIG. 16 is a cross-sectional view of another embodiment of a sheath incorporating the present invention in which the distal expandable portion is formed of a non-elastomeric material.

FIG. 17 is a view similar to that shown in FIG. 16 but showing the cutting blades in extended positions.

In general, the sheath of the present invention is for advancement into a vessel of a human being having a stenosis therein comprising a flexible elongate tubular member having proximal and distal extremities and having a lumen extending therethrough. A portion of the distal extremity of the flexible elongate tubular member is formed so that its distal extremity is expandable so that it can be utilized for enlarging the passageway in a stenosis after the distal extremity of the sheath has been advanced into the stenosis. The sheath is provided with a construction that makes it pushable into the stenosis.

More in particular as shown in the drawings, the sheath 21 with an expandable distal extremity consists of a flexible elongate tubular member 22 having proximal and distal extremities 23 and 24 and with a centrally disposed lumen 26 extending from the proximal extremity to the distal extremity. The flexible elongate member 22 can be of a suitable size, as for example ranging from 0.018" to 0.060" and preferably a size of 3.5 French having an outside diameter of 0.045". However, when utilized in coronary arteries, the size of the sheath can range from 2 to 6 French, whereas in other vessels in the body the sheath can range in sizes as great as 10 French.

The flexible elongate member 22 can have a suitable length as for example to provide a working length of from 130–160 centimeters and preferably 145 centimeters for the sheath 21. With such a construction, the flexible elongate tubular member 22 can have a shaft portion 27 extending from the proximal extremity 23 for a suitable distance, as for example 100 to 110 centimeters and preferably approximately 104 centimeters, and having a lumen size of 0.030" with an outside diameter of 0.045" to provide a wall thickness of 0.006". The shaft portion 27 can be formed of a suitable plastic such as a polyimide.

In order to impart additional pushability and torquability to the shaft portion 27, a cylindrical braid 28 can be incorporated therein as shown in the alternative construction in FIG. 2A. If desired, the braid 28 can extend the entire length of the shaft portion 27. The braid can be formed of a suitable material such as stainless steel in the form of a wire or ribbon having a diameter and a thickness and width ranging from 0.001" to 0.0015". By way of example, such a braid could have a pitch ranging from 80 to 110 and be comprised of 16 braid wires having a diameter of 0.0015" and formed of 304 stainless steel.

The distal extremity of the shaft portion 27 is provided with a plurality of perfusion openings or holes 31 which extend through the sidewall of the shaft portion 27 and which are in communication with the lumen 26. The perfusion holes can be of a suitable size, as for example 0.0135" in diameter. They can be six in number distributed circumferentially along a length of 0.100".

The flexible elongate tubular member 22 also includes an expandable portion 36 which adjoins radiopaque markers 37 and 38 provided on opposite ends of the expandable portion 36. As shown, the radiopaque markers 37 and 38 are in the form of bands formed of radiopaque material so that the position of the expandable portion 36 can be readily ascertained during placement of the sheaths 21 as hereinafter described. The bands 37 and 38 can be formed by radiopaque particles of a suitable material such as radiopaque

4 salts of barium or bismuth which can be embedded or impregnated in the distal extremity of the shaft portion 27 as shown in FIG. 3 and in the proximal extremity of a conical portion 41 forming a part of the flexible elongate tubular member 22. It should be appreciated that the markers 37 and 38, rather than being formed of material impregnated into the plastic forming the shaft portion 27 and the cylindrical end portion 41, can be provided in the form of bands formed of a suitable material such as platinum or gold having a wall thickness of 0.003" and a width of 0.001". One of such bands can be provided on opposite ends of the expandable portion 36 in the same positions as the markers 37 and 38 are provided.

The expandable portion 36 can have a suitable length, as for example 2 to 10 centimeters, and can be formed of a suitable expandable material, such as a non-elastomeric material, so that it cannot be expanded beyond a predetermined size. Alternatively it can be formed of an elastomeric material which is not so limited in its size of expansion. In the embodiment of the invention shown in FIGS. 1 through 4, it has been found to be desirable to use an elastomeric material for the expandable portion 36. In an unexpanded condition, the expandable portion 36 can have an outside diameter substantially the same as the outside diameter of the shaft portion 27 and thus can have a diameter of 0.045" with a lumen 26 extending therethrough having a diameter of 0.030". The end portion 41 can be formed of the same material as the shaft portion 27 and is also provided with a plurality of perfusion holes 42 of the same type as perfusion holes 31 and having the same size and spacing.

The flexible elongate tubular member 22 also includes a conical tip 46 formed of a suitable material such as a soft polyurethane that has a conical outer surface 47 and an opening 48 extending therethrough in communication with the lumen 26. The opening 48 can be of a smaller diameter than the lumen 26, as for example it can have an inside diameter of 0.022", since it is only necessary that it be large enough so that a conventional guide wire 51 can extend therethrough. The conventional guide wire can be of a suitable size as for example 0.010" to 0.18" or larger if desired. The guide wire 51 can be of a conventional construction and therefore will not be described in detail. The shaft portion 27, the expandable portion 36, the end portion 41 and the conical tip 46 of the sheath can be bonded together into a single unitary flexible elongate tubular member 22 in a suitable manner such as by an adhesive or by bonding of the same under heat.

When the expandable portion 36 is formed of an elastomeric material, it is desirable to provide means within the expandable portion 36 providing additional pushability for the expandable portion 36. This is particularly desirable when the expandable portion 36 is formed of an elastomeric material because typically the elastomeric material has a relatively low pushability. For this purpose, a plurality of circumferentially spaced-apart substantially parallel elongate stiffening elements 56 formed of a suitable material such as plastic or stainless steel are embedded in the elastomeric material and extend longitudinally of the expandable portion 36. These elongate elements 56 can be of suitable size, as for example 0.003" in diameter and have a length which extends substantially the entire length of the expandable portion 36.

Alternatively, as shown in FIG. 4A in place of the stiffening elements 56, a cylindrical braid 58 can be incorporated into the elastomeric material forming the expandable portion 36. Such a braid, in order to have the desired amount of flexibility, should have a high pitch as for example a 30 to 60 pitch count, for example a 16-wire braid of the type hereinbefore described.

It is desirable that the flexible elongate tubular member 22 forming the sheath 21 be lubricous so that it can be readily introduced into a vessel with a minimum friction. Thus, for example, it is desirable to place on the outer surface of the shaft portion a lubricous coating 61 formed of a suitable material such as Teflon. In addition it may be desired to provide lubricosity within the lumen 26. This can be accomplished by placing a thin hydrogel coating 62 on the interior surface of the wall forming the lumen 26.

From the construction shown in FIG. 1, it can be seen that the flexible elongate tubular member 22 shown therein has a proximal extremity which can be made to be free of attachments. In order to use the flexible elongate tubular member 22 as a sheath 21 as hereinafter described, it is desirable to provide removable attachments removably secured to the proximal extremity 23 of the flexible elongate tubular member 22. Such removable attachments as shown in FIG. 1 take the form of a Touhy-Borst adapter 66. Such a Touhy-Borst adapter 66 is well known to those skilled in the art and are adapted to be removably secured to the proximal extremity 23 of the flexible elongate tubular member 22 and include a seal 67 which can be compressed into sealing engagement with the proximal extremity 23 to form a high pressure seal therewith by rotation of the cap 68. A hemostasis valve assembly 71 is removably secured to the Touhy-Borst adapter 66. The valve assembly 71 is of a conventional type and includes a resilient seal 72 which by compression by rotation of the threaded cap 73 can form a liquid-tight seal with respect to the guide wire 51 extending therethrough. A side port 76 in communication with the lumen 26 is provided in the assembly 71. The port 76 is connected by flexible tubing 77 formed of a suitable material such as clear plastic connected to a stop cock assembly 78 provided with a tab-like handle 78 adapted to be engaged by the fingers of the hand for moving the stop cock assembly between open and closed positions. The stop cock assembly 78 is provided with a Luer-type fitting 81 which can be connected to another Luer-type fitting for supplying a liquid such as a saline solution to the lumen 26 of the sheath 21.

As hereinafter explained, the sheath 21 can be utilized with conventional angioplasty balloon catheters. However, since such balloon catheters typically are for use with an over-the-wire catheter or are provided with a fixed guide wire, a simplified less expensive balloon catheter can be utilized such as the balloon catheter 91 shown in FIG. 5. As shown therein, the balloon catheter 91 consists of a flexible elongate tubular member 92 having a suitable length, as for example 170 centimeters, and having a diameter of 0.018" to 0.025". It is formed of a suitable plastic such as a polyimide and has proximal and distal extremities 23 and 24 with a flow passage or lumen 96 extending from the proximal extremity to the distal extremity. The lumen 96 can be of a suitable size, as for example 0.010" to 0.012", to provide a sufficiently large lumen so that inflation and deflation of a balloon 97 mounted on the distal extremity thereof can be accomplished in a suitable time period, as for example from 5 to 10 seconds. The balloon 97 typically is a balloon formed of a non-elastomeric material which has a suitable inflated diameter ranging from 1.5 to 5.0 millimeters and preferably approximately 2.0 to 4.0 millimeters.

The flexible elongate tubular member 92 with its balloon 97 can be formed from a single piece of plastic such as polyethylene, Nylon or other notable balloon material. The balloon 97 can be formed in a manner well known to those skilled in the art by inflating the portion of the tubular member 92 which is to be formed into the balloon of the desired size into a mold under heat. It may thereafter be cooled and deflated to collapse into the configuration shown in FIG. 5. The interior of the balloon 97 is in communication with the lumen 96. Alternatively, the balloon 97 can be formed of a different material and then secured to the distal extremity 94 of the flexible elongate tubular member 92 by suitable means such as an adhesive. In both cases, the distal extremity of the balloon 97 is sealed so that the balloon can be inflated with a fluid introduced through the lumen 96. A Luer-type fitting in the form of a removable Touhy-Borst adapter 98 is mounted on the proximal extremity 93 of the flexible elongate tubular member 92 and is adapted to have secured thereto an inflation device 101 of a conventional type which can be utilized for inflating the balloon 97. The balloon catheter 91 to be utilized with the sheath 21 should have a balloon 97 with a length slightly less than the length of the expandable portion 36.

In order to provide additional pushability to the balloon 97, a flexible elongate element 102 formed of a suitable material such as stainless steel having a diameter ranging from 0.003" to 0.006" can be provided having helical coils 103 and 104 on opposite ends. Coil 103 is frictionally secured in the lumen 96 in the flexible elongate tubular member 92 just proximal of the proximal extremity of balloon and permits passage of the inflation medium for the balloon 97 from the lumen 96 into the interior of the balloon 97. The other coil 104 is secured in the distal extremity of the balloon 97 in a suitable fluid-tight seal provided by an adhesive (not shown). A radiopaque marker 105 is mounted on the element 102 equi-distant the ends of the same. Alternatively, a braid (not shown) can be embedded in the balloon 97 to impart improved torquability as well as pushability for the balloon catheter.

Operation and use of the sheath 21 with one or more balloon catheters 91 of various sizes may now be briefly described as follows. Let it be assumed that the sheath 21 has been supplied by a manufacturer with as many as three inexpensive balloon catheters 91 of the type shown in FIG. 5 ranging in balloon sizes of 2.0, 2.5 and 3.5 millimeters, respectively. Also let it be assumed that the sheath 21 has been supplied with the attachments or accessories in the form of a Touhy-Borst adapter 66 and the hemostasis valve assembly 71 being supplied separately as for example in a kit supplied along with the sheath 21. Also let it be assumed that it is desired to perform an angioplasty procedure to increase the size of a flow passage in a stenosis which almost totally or at least substantially blocks the passage of blood in the vessel of the patient. As in a conventional angioplasty procedure, let it be assumed that an opening has been cut into the femoral artery of the patient and that a guiding catheter has been inserted into the femoral artery. Thereafter, a guide wire 51 of a conventional type can be advanced into the guiding catheter until its distal extremity has traversed the stenosis which it is desired to treat, as for example a stenosis 106 which is at least partially occluding the vessel 107. As soon as the guide wire 51 has been advanced to this position, the sheath 21 can be taken and the proximal extremity of the guide wire 51 inserted into the opening 48 and thereafter threaded onto the guide wire and advanced into the guiding catheter over the guide wire so that the guide wire extends through the lumen 26. Because of lubricous qualities of the coating 61, the sheath 21 can be readily advanced over the guide wire until the expandable portion 36 is disposed within the stenosis 106 as for example to the position as shown in FIG. 6. The advancement of the sheath 21 can be observed by the movement of the radiopaque markers 37 and 38.

It should be appreciated that if desired the sheath 21 can have the guide wire 51 threaded into the same and the guide wire and the sheath advanced simultaneously or step by step into the guiding catheter until the guide wire first traverses the stenosis and thereafter is followed by the expandable portion 36 of the sheath 21.

As soon as the distal extremity of the sheath 21 has been advanced through the stenosis, blood can continue to perfuse through the stenosis by passing in through the holes 31 through the lumen 26 and then out the holes 42 on the other side of the stenosis.

As soon as the sheath 21 is in the desired position, the guide wire 51 can be removed. As soon as this has been accomplished, the Touhy-Borst adapter 66 can be mounted on the proximal extremity. A high pressure seal is formed with respect to the proximal extremity by compressing the seal 67 by rotation of the cap 68. Thereafter, the hemostasis valve assembly 71 can be attached to the Touhy-Borst adapter 66. Thereafter, if desired, a saline solution can be supplied to the lumen 26 of the sheath by connecting a suitable source applied to the fitting 81 and opening the stop cock 79 to permit a saline solution to be introduced through the tubing 77 and into the hemostasis valve assembly 71 into the lumen and out the perfusion openings 31 and 42 from opposite sides of the stenosis 106 and out the opening 48.

Prior to or after placement of the Touhy-Borst adapter 66 and the hemostasis valve assembly 71 on the proximal extremity of the flexible elongate member 22, one of the balloon catheters 91 can be introduced directly into the lumen 26 or thereafter by opening the hemostasis valve assembly 71 and by introducing the distal extremity of the balloon catheter 91 through the hemostasis valve assembly and advancing it in the lumen 26 until it has been advanced into the expandable portion 36 of the sheath 21 and so that it is also disposed of in the stenosis 106. Pushability of the balloon 97 is enhanced by the presence of the flexible elongate element 102 in the balloon 97 to provide column strength. With the balloon 97 in a deflated condition, blood will continue to perfuse past the balloon 97 into the openings 31 and out through the openings or holes 42.

As soon as the balloon catheter is in the desired position, the inflation device 101 can be attached to the fitting 98 and the balloon 97 inflated for example by placing a radiopaque contrast liquid into the interior of the balloon through the lumen 96 to cause the balloon 97 formed of a non-elastomeric material to expand and to thereby expand the expandable portion 36 of the sheath 21 to compress the plaque 106 and to form a larger flow passage 108 through the stenosis formed by the plaque 106.

The expandable portion 36 can be expandable one or more times by successfully inflating and deflating the balloon 97 by use of the inflation device 101. The inflation and deflation times for the balloon 97 are relatively short as for example within 5 to 10 seconds because of the relatively large size of the lumen 96 for inflating the balloon 97. As soon as the balloon 97 is deflated, blood can continue to perfuse through the sheath 21 in the manner hereinbefore described. Thereafter, the balloon catheter 91 can be removed.

Let it be assumed that it is desired to form a still larger passage through the stenosis 106. This can be accomplished in a rapid exchange fashion because after the removal of a balloon catheter 91 of one size, another balloon catheter 91 of a larger size can be readily introduced in the sheath 21 in the manner hereinbefore described for the previous balloon catheter 91 and the balloon thereon 97 inflated to increase the expansion of the expandable portion 36 to still further compress the plaque of the stenosis 106 and to thereby form a still larger passage 108 through the stenosis. The balloon 97 can be repeatedly inflated and deflated. If it is desired to still utilize a still larger balloon catheter 91, the balloon catheter 91 in place can be readily deflated and removed followed by insertion of another balloon catheter 91 followed by inflation and deflation of the balloon 97 of the additional balloon catheter to increase the passage 108 through the stenosis 106 to the desired size.

From the foregoing, it can be seen that the sheath 21 serves as a rapid exchange sheath permitting the rapid exchange of different size balloon catheters. The distal extremity of the sheath 21 remains in the stenosis so that the larger size balloon catheters can be readily introduced into the expandable portion 36 of the sheath 21. By use of such a rapid exchange sheath, it can be seen that the necessity for using a rapid exchange balloon catheter is eliminated. Also it can be seen that with the use of the sheath with an expandable distal extremity, it is possible to utilize relatively inexpensive balloon catheters to reduce the cost of an angioplasty procedure.

After the flow passage 108 is increased to the desired size, the balloon 97 can be deflated and thereafter, the balloon catheter 91 can be removed separately or removed as a unit with the sheath 21, after which the femoral artery can be closed in a conventional manner.

In FIGS. 7A, 7B and 7C there are shown illustrations showing how the sheath 21 of the present invention can be utilized for delivering an expandable stent 116 of a conventional type into a stenosis 106. Thus as shown, the stent 116 can be placed over the expandable portion 36 of the sheath 21 and frictionally retained thereon and advanced over a guide wire 51 which has traversed the stenosis in the manner hereinbefore described so that the expandable portion 36 with the stent 116 carried thereby is disposed in the stenosis. Thereafter as shown in FIG. 7B, a balloon catheter 91 of the type hereinbefore described can be advanced into the sheath 21 so that its balloon 97 is disposed within the expandable portion 36 to cause expansion of the stent 116 and also at the same time to cause compression of the plaque forming the stenosis 106 as shown in FIG. 7B. Prior to inflation of the balloon catheter 91 within expandable portion 36, it can be seen that blood can perfuse through the stenosis by passing into the holes 31 and out the holes 42. As soon as the stent has been expanded so that it is disposed within the stenosis and frictionally engages the stenosis 106, the balloon catheter 91 can be deflated causing the expandable portion 36 to collapse as shown in FIG. 7C permitting blood to perfuse through the holes 31 and 42 and also to flow past the expandable portion 36 as shown in FIG. 7C. The balloon catheter 91 and the sheath 21 can then be removed leaving the stent 116 in place within the stenosis and hopefully precluding restenosis in the vessel in that location.

FIGS. 8A through 8D illustrate the manner in which the sheath 21 with the expandable distal extremity can be utilized for placement of a self-expanding stent 121. The self-expanding stent 121 can be of a type well known to those skilled in the art and is friction retained on the expandable portion 36 as shown in FIG. 8A. In order to prevent the self expansion of the sheath 121, a sleeve 126 of a suitable lubricous plastic material such as Teflon is utilized having a wall thickness of 0.002" to 0.015" and having proximal and distal extremities 27 and 28 with the distal extremity being disposed over and enclosing the self-expanding stent 121 to prevent expansion of the same. The proximal extremity is provided with the fitting 129 of a suitable type so that the sleeve 126 can be grasped by the hand to facilitate removal of the same. Thus the sheath 21 with the self-expanding stent mounted on the expandable portion 36 and held in place by the sleeve 126 can be advanced over the guide wire 51 into the stenosis 106. The guide wire 61 can then be removed. Also the Touhy-Borst adapter 66 can be removed from the proximal extremity 23 of the flexible elongate tubular member 22 so that the sleeve 126 can be retracted permitting the distal extremity of the self-expanding stent 121 to begin expanding as shown in FIG. 8B. Thereafter, the sleeve 126 can be completely removed so that it clears the self-expanding stent 121 permitting the self-expanding stent 121 to frictionally engage the stenosis 106 and to be retained therein.

Let it be assumed that it is desired to form a still larger passage 108 through the stenosis than that provided by the forces of the self-expanding stent 121. To accomplish this, a balloon catheter 91 of the type hereinbefore described is advanced through the hemostasis valve assembly 71 (not shown) through the Touhy-Borst adapter 66 and into the lumen 26 of the sheath 21 until the balloon 97 of the balloon catheter 91 is disposed in the expandable portion 36 of the sheath 21. Thereafter, the balloon 97 can be inflated in the manner hereinbefore described to cause expansion of the expandable portion 36 to cause the self-expanding stent 121 to expand still further and to form a larger passageway through the stenosis 106. After the self-expanding stent 121 has been expanded the desired amount, the balloon 97 can be deflated and the balloon catheter 91 removed. The expandable portion 36 collapses permitting the sheath 21 to be removed.

As shown in FIGS. 9A and 9B, in place of the sleeve 126 which must be removed proximally from the sheath 21, a splittable sleeve 131 which can be mounted on the sheath 21 and has distal extremity (not shown) extend over the self-expanding stent 121. When the self-expanding stent 121 has been advanced into the stenosis 106 and it is desired to permit it to expand, the splittable sleeve 131 can be readily removed by grasping the separate finger handles 132 and 133 provided on the proximal extremity of the same and pulling them apart by the fingers of the hand to cause the sleeve 131 to split on opposite sides longitudinally of the sleeve so that the sleeve 131 can be pulled proximally and progressively split apart so that its distal extremity clears the self-expanding stent 121 to permit it to expand into and frictionally engage the stenosis 106. The entire splittable sleeve can be split apart and removed without removal of the Touhy-Borst adapter 66 or any other attachments which may be present on the proximal extremity of the sheath 121. After the sleeve 131 has been removed, the self-expanding sheath 121 can be further expanded in the manner hereinbefore described after which the sheath 21 can be removed.

Another embodiment of a sheath incorporating the present invention is the sheath 151 is shown in FIG. 10 and consists of a flexible elongate tubular member 152 formed of a suitable plastic hereinbefore described which is provided with proximal and distal extremities 153 and 154 and a lumen 156 extending from the proximal extremity 153 to the distal extremity 154. It is constructed in a manner very similar to the embodiments hereinbefore described. However, it consists of shaft portions 152a and 152b with the shaft portion 152a being approximately 104 centimeters long and being formed of a braided polyimide with 80–110 pitch count and portion 152b being approximately 30 centimeters in length formed of a braided polyimide having 210–280 pitch count. There is also provided with a portion 152c having perfusion holes 158 therein open to the central lumen 156 permitting blood to perfuse through a portion 152d which is an expandable portion and another portion 152e having outlet holes 159 formed therein in communication with the lumen 156. It is also provided with a conical portion 152f which is relatively soft and pliable. In addition, radiopaque markers 161 and 162 of the type hereinbefore described are disposed proximally and distally of the inflatable portion 152d. The braids are utilized to provide the desired pushability and torquability for the sheath 151. The expandable portion 152D is also provided with a braid to give the desired pushability to the sheath.

In the embodiment of the sheath 151 shown in FIGS. 10 and 11, there is provided means for cutting the plaque 106 so as to break it apart in the event it calcified so it is relatively hard and cannot be readily compressed or expanded by the mere force of the balloon catheter 91 hereinbefore described. For this purpose, a plurality of cutting blades 156 have been provided which are mounted in the material forming the expandable portion 152d. As shown in FIGS. 10 and 11, the blades 166 can be formed of a suitable material such as stainless steel having a length of approximately 2 centimeters and having a blade thickness of 0.005" and a height of 0.01". The blades are provided with cutting edges 167 which are triangular in cross section as shown in FIG. 11. Each of the blades 166 is provided with a foot portion 166a which is seated in the material as for example the elastomeric material forming the expandable portion 152d. As shown in FIG. 11 before expansion of the expandable portion 152d, the cutting edges 167 of the blade 166 are disposed just below the circumferential surface 168 of the expandable portion 152d.

Operation and use of the sheath 151 as shown in FIGS. 10 and 11 may now be described. The sheath can be advanced over a guide wire 51 in the same manner in which the sheath 21 was advanced into the stenosis 106. After the expandable portion 152d of the sheath 151 has been advanced into the stenosis 106, a balloon catheter 91 of the type hereinbefore described can be advanced into the sheath 151 so that its balloon 97 is in registration with the stenosis 106. Expansion of the balloon 97 causes the cutting edges 167 of the cutting blades 166 to pierce the outer circumferential surface 168 of the expandable portion 152d to extend radially therefrom and to cut longitudinally extending slits into the plaque forming the stenosis 106. If desired, the balloon 97 can be deflated and the distal extremity of the sheath 151 rotated after which the balloon 97 again can be inflated to cause additional cuts or slits to be made in the plaque forming the stenosis 106. After sufficient slits have been made, the balloon 97 can be deflated after which the expandable portion 152 will collapse bringing inwardly the blades 166 so that they no longer penetrate through the circumferential surface 168 after which the sheath 151 can be removed.

If it is believed that there is danger that the blades 166 may not be fully retracted and may cause cutting of the vessel wall during retraction of the sheath 151, a sleeve (not shown) of a suitable flexible material may be advanced over the sheath 151 until it covers the blades 166 after which the sheath 151 along with the cover can be removed.

Another embodiment of a sheath having recessed cutting blades is shown in FIGS. 14 and 15 which correspond to FIGS. 11 and 13. Thus as shown in FIG. 14 there is provided a sheath 171 having an expandable sheath portion 171a which is formed of an elastomeric material that is provided with longitudinally extending arcuate recesses 176 extending longitudinally thereof which have mounted therein the blades 166 mounted in those recesses with the cutting edges 167 being recessed below the peripheral surface of the portion 171a as shown in FIG. 14. As soon as the expandable portion 171a is expanded by the use of a balloon catheter in the manner hereinbefore described, the cutting edges 167 are advanced so that they extend around the peripheral surface of the portion 171a and cut slits into the plaque forming the stenosis 106. Additional slits can be made in the manner hereinbefore described with the embodiment shown in FIGS. 11, 12 and 13. After the desired amount of cuts have been formed in the plaque, the balloon can be deflated after which the portion 171a will collapse permitting the sharp cutting edges 167 to be retracted so that they cannot cut the vessel wall when the sheath 171 is retracted from the vessel. Again, if desired to protect the vessel, the sheath 171 can be provided with a sleeve (not shown) covering the cutting edges 167 prior to the time that the sheath 171 is removed.

Another embodiment of the sheath incorporating the present invention shown in FIGS. 16 and 17 in which a sheath 181 is provided with an inflatable distal extremity provided by a non-elastic expandable portion 181a in which longitudinally extending portions 181b are folded in a clockwise direction and carry within the folds cutting blades 186 of the type hereinbefore described. These blades 186 are protected by the folds 181b of the expandable portion 181a. When the expandable portion 181a is expanded by a balloon catheter 91 of the type hereinbefore described, the folds 181b unfold to form a circle in cross section and to move the cutting blades 186 carried thereby outwardly in a radial direction to cause slits to be formed in the plaque of the stenosis 106 in the manner hereinbefore described. Additional slits also can be formed also in the manner hereinbefore described. After the slits have been formed, the balloon 97 of the balloon catheter 91 can be deflated and removed. Deflation of the balloon will cause collapse of the expandable portion 181a causing the folds 181b to be made to cover the blades 186.

From the foregoing it can be seen that there has been provided a sheath with an expandable distal extremity which has many advantages particularly when performing medical procedures such as angioplasty procedures. The sheath has sufficient stiffness and/or column strength so that it can be advanced on its own over a guide wire into a stenosis. It is provided with holes therein communicating with the lumen within the sheath thereby permitting perfusion of blood across the stenosis when the expandable portion of the sheath is in position and the stenosis. The sheath because of its construction makes it possible the rapid exchange of various sizes of balloon catheters without losing the desired position within the stenosis within the vessel of the patient this makes it possible to utilize several balloons of different sizes to enlarge the flow passage through the stenosis. In order to inhibit restenosis, a stent can be carried by the inflatable portion of the piece and then expanded into position within the stenosis after which the sheath can be removed. Expandable and self-expanding sheaths can be utilized. Additionally, for particularly calcified stenoses in vessels, the expandable portion of the sheath can be provided with longitudinally extending cutting blades which can be yieldably urged into engagement with the plaque forming the stenosis to form slits in the stenosis to more readily facilitate expansion of the flow passage through the stenosis.

The sheath in addition to having the desired pushability also has the necessary torquability to make it possible to advance the sheath through tortuous vessels over the guide wire. The sheath is lubricous so that it can be readily advanced through the vessel with a minimum of resistance and trauma to the vessel through which it is being introduced. The attachments or accessories provided for the proximal extremity of the sheath are removable so that removable sleeves can be provided on the exterior of the sheath when necessary. The hemostasis valve prevents blood from leaking out during the procedure. The sheath is constructed in such a manner so that it can be constructed inexpensively. It can be formed utilizing a single part construction or a multi-part construction as hereinbefore described. The use of the sheath with the balloon catheters greatly reduces the cost of angioplasty procedure.

Although the foregoing sheath and the method of using the same may have been described principally in connection with angioplasty procedures, it is readily apparent that the sheath and the balloon catheters for use therewith can be utilized in other vessels in the body as for example arteries and veins.

We claim:

1. A sheath for advancement into a vessel of a body of a patient having a stenosis therein which at least partially occludes the flow of blood in the vessel and is for use with a plurality of balloon catheters having distal extremities with inflatable balloons thereon with the balloon on one of the plurality of catheters having an inflated size greater than the inflated size of another of the plurality of catheters comprising a flexible elongate tubular member formed of plastic and having proximal and distal extremities and having a lumen extending from the proximal extremity to the distal extremity sized to receive one at a time of said plurality of balloon catheters, a portion of the distal extremity of the flexible elongate tubular member overlying the region in which the inflatable balloon of one of the plurality of balloon catheters is normally positioned being formed so that it is radially expandable and means carried by the expandable portion for imparting pushability and column strength to the expandable portion and an attachment mounted on the proximal extremity of the flexible elongate tubular member, said flexible elongate tubular member having a length so that when the expandable portion is disposed in the stenosis, the proximal extremity with the attachment thereon is outside the body of the patient and the lumen in the proximal extremity is accessible for introduction of the balloon catheters into the lumen of the sheath one at a time from a location exterior of the body, the radial expansion of the distal extremity of the flexible elongate tubular member being caused by expansion of at least one of the inflatable balloons of the plurality of balloon catheters.

2. A sheath as in claim 1 wherein said expandable portion is formed of an elastomeric material.

3. A sheath as in claim 1 wherein said expandable portion is formed of a non-elastomeric material.

4. A sheath as in claim 1 further including mesh means embedded within the plastic to provide increased pushability and torquability for the flexible elongate tubular member over that it would have without the mesh means embedded therein.

5. A sheath as in claim 1 wherein said attachment is in the form of attachment means removably secured to the proximal extremity of the sheath for permitting introduction of one of the plurality of balloon catheters through the attachment means and forming a fluid-tight seal with respect thereto and permitting said one balloon catheter with the balloon thereon to be advanced so that the balloon is disposed in the inflatable portion of the sheath.

6. A sheath as in claim 1 in combination with a stent carried by the inflatable portion of the sheath.

7. A sheath combination as in claim 6 wherein said stent is expandable.

8. A sheath combination as in claim 7 wherein said stent is self expandable.

9. A sheath combination as in claim 8 together with a removable sleeve extending over the sheath and over the self expandable stent.

10. A sheath combination as in claim 9 wherein said removable sleeve is provided with a proximal extremity adjacent the proximal extremity of the sheath and is adapted to be grasped.

11. A sheath combination as in claim 10 wherein said removable sleeve is splittable facilitating removal of the sleeve to expose the self expandable stent without removal of the removable attachment means.

12. A sheath as in claim 1 further including a plurality of circumferentially spaced apart longitudinally extending cutting blades carried by the expandable portion of the sheath.

13. A sheath as in claim 12 wherein said cutting blades have cutting edges which are recessed within the confines of the expandable portion.

14. A sheath as in claim 12 further including a removable sleeve extending over the cutting blades.

15. A sheath for advancement into a vessel of a patient having a stenosis therein which at least partially occludes the flow of blood in the vessel and is for use with a plurality of balloon catheters having distal extremities with an inflatable balloon thereon with the balloon on one of the plurality of catheters having an inflated size greater than the inflated size of another of the plurality of catheters comprising a flexible elongate tubular member formed of plastic and having proximal and distal extremities and having a lumen extending from the proximal extremity to the distal extremity sized to receive one at a time of said plurality of balloon catheters, a portion of the distal extremity of the flexible elongate tubular member being imperforate and being formed so that it is radially expandable and means carried by the expandable portion for imparting pushability and column strength to the expandable portion and an attachment mounted on the proximal extremity of the flexible elongate tubular member, said flexible elongate tubular member having a length so that when the expandable portion is disposed in the stenosis, the proximal extremity with the attachment thereon is outside the vessel of the patient, said means carried by the expandable portion of the sheath including a plurality of stiffening elements spaced circumferentially around the expandable portion and extending longitudinally substantially the entire length of the expandable portion.

16. A sheath as in claim 15 wherein said stiffening elements are in the form of a plurality of discrete elongate elements.

17. A sheath for advancement into a vessel of a patient having a stenosis therein which at least partially occludes the flow of blood in the vessel and is for use with a plurality of balloon catheters having distal extremities with an inflatable balloon thereon with the balloon on one of the plurality of catheters having an inflated size greater than the inflated size of another of the plurality of catheters comprising a flexible elongate tubular member formed of plastic and having proximal and distal extremities and having a lumen extending from the proximal extremity to the distal extremity sized to receive one at a time of said plurality of balloon catheters, a portion of the distal extremity of the flexible elongate tubular member being imperforate and being formed so that it is radially expandable and means carried by the expandable portion for imparting pushability and column strength to the expandable portion and an attachment mounted on the proximal extremity of the flexible elongate tubular member, said flexible elongate tubular member having a length so that when the expandable portion is disposed in the stenosis, the proximal extremity with the attachment thereon is outside the vessel of the patient, said means carried by the expandable portion being in the form of a braid embedded in the expandable portion.

18. A sheath for advancement into a vessel of a patient having a stenosis therein which at least partially occludes the flow of blood in the vessel and is for use with a plurality of balloon catheters having distal extremities with an inflatable balloon thereon with the balloon on one of the plurality of catheters having an inflated size greater than the inflated size of another of the plurality of catheters comprising a flexible elongate tubular member formed of plastic and having proximal and distal extremities and having a lumen extending from the proximal extremity to the distal extremity sized to receive one at a time of said plurality of balloon catheters, a portion of the distal extremity of the flexible elongate tubular member being imperforate and being formed so that it is radially expandable and means carried by the expandable portion for imparting pushability and column strength to the expandable portion and an attachment mounted on the proximal extremity of the flexible elongate tubular member, said flexible elongate tubular member having a length so that when the expandable portion is disposed in the stenosis, the proximal extremity with the attachment thereon is outside the vessel of the patient, said flexible elongate tubular member being provided with holes proximal and distal of the expandable portion permitting perfusion of blood into the lumen, through the expandable portion and out of the lumen.

19. The combination for use in a vessel of a patient having a stenosis therein which at least partially occludes the flow of blood in the vessel of a sheath and a plurality of balloon catheters, each of the balloon catheters having a proximal extremity and a distal extremity with a balloon carried by the distal extremity with one of the balloon catheters being disposed in the sheath, the sheath comprising a flexible elongate tubular member formed of plastic and having proximal and distal extremities and having a lumen extending from the proximal extremity to the distal extremity sized to receive one at a time of said plurality of balloon catheters, a portion of the distal extremity of the flexible elongate tubular member overlying the balloon of said one balloon catheter being formed so that it is radially expandable and means carried by the expandable portion for imparting pushability and column strength to the expandable portion and an attachment mounted on the proximal extremity of the flexible elongate tubular member, said flexible elongate tubular member having a length so that when the expandable portion is disposed in the stenosis, the proximal extremity with the attachment thereon is outside the vessel of the patient and means secured to the proximal extremity of said one balloon catheter for inflating the balloon and thereby causing expansion of the expandable portion of the sheath whereby when the expandable portion of the sheath is disposed in the stenosis a flow passage of increased size is formed in the stenosis as the expandable portion is expanded, the radial expansion of the distal extremity of the flexible elongate tubular member being caused by expansion of at least one of the inflatable balloons of the plurality of balloon catheters.

20. A method for forming a larger flow passage in a stenosis in a vessel in the body of a patient by the use of a guide wire, a plurality of balloon catheters having distal extremities with inflatable balloons thereon with the balloon on one of the catheters having an inflated size greater than the inflated size of another of the balloon catheters and a substantially imperforate sheath with an expandable distal extremity and having a lumen extending from the proximal extremity to the distal extremity and being sized to receive one at a time of said plurality of balloon catheters, a portion of the distal extremity of the flexible elongate tubular member being imperforate and being formed so that it is radially expandable, the sheath having a proximal extremity and an attachment secured to the proximal extremity and having a length ranging from 130–160 centimeters comprising the steps of advancing the guide wire through the stenosis, advancing the sheath with an expandable distal extremity over the guide wire from outside the body so that the expandable distal extremity is moved into registration with the stenosis while retaining the proximal extremity with the attachment thereon outside the body, advancing on of the balloon catheters into the sheath from outside the body so that the balloon thereon is in registration with the expandable portion of the sheath, inflating the balloon thereon to cause expansion of the expandable portion of the sheath to increase the size of the flow passage in the stenosis, deflating the balloon thereon and removing said one balloon catheter from the sheath and if required advancing another of the balloon catheters of a larger inflated size into the sheath from outside the body while the expandable portion of the sheath is still disposed within the stenosis, inflating the balloon of the another balloon catheter to cause expansion of the expandable portion to cause a still further enlargement of the flow passage through the stenosis, deflating the balloon of the another balloon catheter and removing the another balloon catheter from the sheath and removing the sheath.

21. A method as in claim 20 further including removing the guide wire prior to the introduction of the balloon catheter into the sheath.

22. A method as in claim 20 together with a stent carried by the expandable portion of the sheath, wherein the stent is advanced into the stenosis from outside the body at the time that the expandable portion is advanced into the stenosis from outside the body and permitting the stent to expand into engagement with the stenosis and thereafter removing the sheath.

23. A method as in claim 20 wherein the sheath carries cutting elements carried by the expandable portion of the sheath and wherein the cutting elements are urged into engagement with the stenosis upon expansion of the balloon of the balloon catheter to form slits in the stenosis.

* * * * *